US007815911B1

(12) United States Patent
Straley et al.

(10) Patent No.: US 7,815,911 B1
(45) Date of Patent: Oct. 19, 2010

(54) **COMPOSITIONS AND METHODS FOR TREATING *YERSINIA PESTIS* INFECTION**

(75) Inventors: Susan C. Straley, Lexington, KY (US); Brian S. Murphy, Lexington, KY (US); Stanislav Forman, Santa Ana, CA (US); Christine R. Wulff, Columbia, SC (US); Robert D. Perry, Lancaster, KY (US); Tanya Myers-Morales, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 152 days.

(21) Appl. No.: 11/870,315

(22) Filed: Oct. 10, 2007

Related U.S. Application Data

(60) Provisional application No. 60/828,895, filed on Oct. 10, 2006.

(51) Int. Cl.
| | |
|---|---|
| *A61K 39/00* | (2006.01) |
| *A61K 39/38* | (2006.01) |
| *A61K 39/02* | (2006.01) |
| *A61K 45/00* | (2006.01) |
| *A61K 38/00* | (2006.01) |
| *A01N 37/18* | (2006.01) |

(52) U.S. Cl. ............. 424/192.1; 424/184.1; 424/185.1; 424/190.1; 424/234.1; 424/242.1; 424/278.1; 514/2; 514/12

(58) Field of Classification Search ............... None
See application file for complete search history.

(56) References Cited

U.S. PATENT DOCUMENTS

| | | | | |
|---|---|---|---|---|
| 5,985,285 | A * | 11/1999 | Titball et al. ............. | 424/234.1 |
| 6,706,522 | B1 * | 3/2004 | Blattner et al. ............ | 435/320.1 |
| 6,964,770 | B2 * | 11/2005 | Brubaker et al. .......... | 424/234.1 |
| 7,344,718 | B2 * | 3/2008 | Nilles et al. .............. | 424/184.1 |
| 7,572,449 | B2 * | 8/2009 | Hill et al. ................. | 424/164.1 |
| 2004/0151727 | A1 * | 8/2004 | Nilles et al. .............. | 424/184.1 |
| 2005/0136075 | A1 * | 6/2005 | Mecsas et al. ............ | 424/234.1 |
| 2005/0220797 | A1 * | 10/2005 | Chanh et al. ............. | 424/164.1 |
| 2005/0232940 | A1 * | 10/2005 | Brubaker et al. ......... | 424/190.1 |
| 2006/0093609 | A1 * | 5/2006 | Hill et al. ................. | 424/164.1 |
| 2006/0246084 | A1 * | 11/2006 | Brubaker et al. ......... | 424/184.1 |

FOREIGN PATENT DOCUMENTS

WO    WO 2009/009759 A2  *  11/2009

OTHER PUBLICATIONS

Chain et al, PNAS, Sep. 21, 2004, 101/38:13826-13831.*
Titball et al, Expert Opin. Biol. Ther., 2004, 4/6:965-973.*
Williamson, J. Applied Microbiology, 2001, 91:606-608.*
Heath et al, Vaccine, 1998, 16(11/12):1131-1137.*
Parkhill et al, Nature, 2001, 413(6855):523-527.*
Deng et al, J. Bacteriology, Aug. 2002, 184/16:4601-4611.*
Straley et al, Trends in Microbiol., 1995, 3/8:310-317.*
Burgess et al, JCB, 1990, 111:2129-2138.*
Lazar et al, Molecular and Cellular Biology, 1988, 8:1247-1252.*
Creighton, In: Proteins Structures and Molecular Properties, 1984, pp. 314-315.*
Greenspan et al, Nature Biotechnology, 1999, 17:936-937.*
Houghten et al, Vaccine86, 1986, pp. 21-25.*
Bixler et al, Synthetic Vaccines, 1987, 1:39-71.*
Bowie et al, Science, 1990, 247:1306-1310.*
Kumar et al, PNAS, 87:1337-1341.*
Creighton, In: Protein Structure, A Practical Approach, 1989, pp. 184-186.*
Nosoh et al, In: Protein Stability and Stabilization through Protein Engineering, 1991, chapter 7, pp. 198-215.*
Chain et al, J. Bacteriology, Jun. 2006, 188/12:4453-4463.*
Neyt et al, Molecular Microbiology, 1999, 61/1:143-156.*
Wilharm et al, Protein Expression and Purification, 2003, 31:167-172.*
Forman, et al.; yadBC of *Yersinia pestis*, a New Virulence Determinant for Bubonic Plague; Infection and Immunity; 2008; pp. 578-587.

* cited by examiner

*Primary Examiner*—N. M. Minnifield
(74) *Attorney, Agent, or Firm*—Stites & Harbison PLLC; Mandy Wilson Decker (57) ABSTRACT

Compositions and methods for treating a *Yersinia pestis* (*Y. pestis*) infection are provided. Compositions and methods of for inducing an immune response in a subject are provided. Composition can include a YadC polypeptide.

10 Claims, 5 Drawing Sheets

COMPOSITIONS AND METHODS FOR TREATING *YERSINIA PESTIS* INFECTION

RELATED APPLICATIONS

This application claims priority from U.S. Provisional Application Ser. No. 60/828,895 filed Oct. 10, 2006, the entire disclosure of which is incorporated herein by this reference.

GOVERNMENT INTEREST

Subject matter described herein was made with U.S. Government support under Grant Number AI48491, IUF4 AI057175, and 5K30HL004163-05 awarded by the National Institute of Allergy and Infectious Diseases of the National Institute of Health. The United States government has certain rights in the subject matter.

TECHNICAL FIELD

The presently-disclosed subject matter relates to compositions and methods for preventing and/or treating plague, including compositions and methods for preventing and/or treating infection by *Yersinia pestis*.

INTRODUCTION AND GENERAL CONSIDERATIONS

*Yersinia pestis* is a highly virulent extracellular pathogen, which causes lethal infection in humans and other animals. *Y. pestis* infection causes plague, including bubonic, pneumonic, and septicemic plague. The bacterium poses an ominous threat as an agent of bioterrorism. It is highly infectious and contagious by aerosol and can kill in as little as two days after exposure.

*Y. pestis* can be categorized into sub-types, including: Antigua, Medievalis, and Orientalis. *Y. pestis* pathogenicity can be blocked by antibodies to two protein antigens, the capsule subunit Caf1 (also known as F1 antigen, or Fraction 1 antigen), and a surface protein called V antigen (also known as LcrV). In this regard, compositions including the F1 antigen and the V antigen have been studied for use in treating and preventing *Y. pestis* infection. Although such compositions have been shown to offer modest protection, against some strains of *Y. pestis*, there are many virulent strains of *Y. pestis*. Examples of such strains include, for example, strain KIM of the Mediaevalis sub-type, and strain CO92 of the Orientalis sub-type. Additionally, modifications to *Y. pestis* antigens can be made without destroying virulence. For example, the V-antigen is variable, such that known compositions containing the V-antigen may not be fully protective against certain modified strains. Furthermore, the F1 antigen is not required for virulence in pneumonic plague, and its gene is easily deleted, posing the potential of a weaponized F1-lacking *Y. pestis* against which known compositions containing F1 antigen are not effective.

Accordingly, there remains a need in the art for compositions and methods for preventing and/or treating various types and strains of *Y. pestis* infection.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compositions and methods for treating a *Yersinia pestis* (*Y. pestis*) infection (or plague resulting from such an infection). Compositions and methods of the presently-disclosed subject matter can be used for inducing an immune response in a subject.

In some embodiments, compositions include an isolated polypeptide molecule comprising a sequence at least 80%, 85%, 90%, or 95% identical to SEQ ID NO: 1, or a functional fragment thereof. In some embodiments, the isolated polypeptide molecule comprises a sequence at least 80%, 85%, 90%, or 95% identical to SEQ ID NO: 3. In some embodiments, the isolated polypeptide molecule comprises the sequence of SEQ ID NO: 3.

In some embodiments, compositions include an isolated polypeptide molecule comprising a sequence at least 80%, 85%, 90%, or 95% identical to an amino acid sequence including residues 137-345 of SEQ ID NO: 1. In some embodiments, compositions include an isolated polypeptide molecule comprising a sequence at least 80%, 85%, 90%, or 95% identical to an amino acid sequence including residues 137-345 of SEQ ID NO: 1. In some embodiments, compositions include an isolated polypeptide molecule comprising a sequence at least 80%, 85%, 90%, or 95% identical to an amino acid sequence including residues 32-345 of SEQ ID NO: 1.

In some embodiments, compositions include an isolated polypeptide molecule comprising an amino acid sequence including residues 32-345 of SEQ ID NO: 1. In some embodiments, compositions include an isolated polypeptide molecule comprising an amino acid sequence including residues 32-409 of SEQ ID NO: 1. In some embodiments, compositions include an isolated polypeptide molecule comprising an amino acid sequence including residues 32-409 of SEQ ID NO: 1.

In some embodiments, compositions include an isolated polypeptide molecule comprising a sequence at least about 80%, 85%, 90%, or 95% identical to an amino acid sequence of SEQ ID NO: 1, wherein up to about 5, 10, 15, 20, 25, 30, 50, 125, or 150 amino acids are truncated from the N-terminus of SEQ ID NO: 1. In some embodiments, the isolated polypeptide molecule comprises at least about 200, 210, 225, 235, 245, 255, 265, 275, 285, 295, 300, 325, 350 or 375 amino acids of SEQ ID NO: 1.

In some embodiments, compositions include an isolated polypeptide molecule comprising a sequence at least about 80%, 85%, 90%, or 95% identical to an amino acid sequence of SEQ ID NO: 1, wherein up to about 10, 50, 75, 100, 150, 175, 200, 225, 250, 275, 300, 325, 350, or 400 amino acids are truncated from the C-terminus of SEQ ID NO: 1. In some embodiments, the isolated polypeptide molecule comprises at least about 200, 210, 225, 235, 245, 255, 265, 275, 285, 295, 300, 325, 350 or 375 amino acids of SEQ ID NO: 1.

In some embodiments, compositions comprise an polypeptide molecule encoded by a nucleotide sequence at least about 80, 85, 90, or 95% identical to SEQ ID NO: 2, or a subsequence thereof. The encoded polypeptide has improved immune response activity relative to, or has all or some of the immune response activity of, a polypeptide encoded by a nucleotide sequence of SEQ ID NO: 2. In some embodiments, the polypeptide molecule is encoded by a subsequence of the nucleotide sequence of SEQ ID NO: 2, wherein up to about 15, 30, 45, 60, 75, 90, 150, 375, or 450 nucleotide residues are truncated from the 5' terminus of SEQ ID NO: 2. In some embodiments, the polypeptide molecule is encoded by a subsequence of the nucleotide sequence of SEQ ID NO: 2, wherein up to about 30, 150, 225, 300, 450, 525, 600, 675, 750, 825, 900, 975, 1050, or 1200 nucleotide residues are truncated from the 3' terminus of SEQ ID NO: 2.

In some embodiments, compositions include a conservatively-substituted variant of the polypeptide molecule of SEQ ID NO: 1, or functional fragments thereof. In some embodiments, compositions include a conservatively-substituted variant of the polypeptide molecule of SEQ ID NO: 3, or functional fragments thereof.

In some embodiments, the polypeptide molecule includes the amino acid sequence of SEQ ID NO: 1, or a subsequence thereof, with up to about 1, 2, 3, 4, 5, 6, 7, 8, 9, 10, 15, 20, or 25 conservative amino acid substitutions. In some embodiments, the polypeptide molecule includes the amino acid sequence of SEQ ID NO: 3, or a subsequence thereof, with up to about 1, 2, 3, 4, 5, 6, 7, 8, 9, 10, 15, 20, or 25 conservative amino acid substitutions. In some embodiments, the conservative amino acid substitutions are at or between residues 346-622 of the YadC polypeptide of SEQ ID NO: 1, or a subsequence thereof. In some embodiments, the polypeptide molecule includes the amino acid sequence of SEQ ID NO: 1, or a subsequence thereof, with up to about 1, 2, 3, 4, or 5 conservative amino acid substitutions are at or between residues 32-345 of the YadC polypeptide of SEQ ID NO: 1, or a subsequence thereof.

In some embodiments, compositions induce an immune response in a subject against F1-positive and F1-negative strains of *Y. pestis*. In some embodiments, compositions induce an immune response in a subject against F1-negative strains of *Y. pestis*. In some embodiments, the subject is in need of treatment for a *Y. pestis* infection. In some embodiments, the subject is susceptible to *Y. pestis* infection.

In some embodiments, methods include administering to a subject a composition including a YadC polypeptide, as described herein. The composition can be administered in an amount sufficient to induce an immune response in the subject. The presently-disclosed subject matter includes methods for treating a *Yersinia pestis* (*Y. pestis*) infection and/or treating a plague resulting from such an infection, including administering to the subject an effective amount of a composition including a YadC polypeptide, as described herein. In some embodiments, methods include introducing into a subject a composition comprising an isolated polypeptide molecule comprising an amino acid sequence of SEQ ID NO: 1, or a functional fragment thereof. In some embodiments, methods include introducing into a subject a composition comprising an isolated polypeptide molecule comprising an amino acid sequence of SEQ ID NO: 3, or a functional fragment thereof. In some embodiments, methods include introducing into a subject a composition comprising a sequence at least 80, 85, 90, or 95% identical to SEQ ID NO: 1, or a functional fragment thereof. In some embodiments, methods include introducing into a subject a composition comprising a sequence at least 80, 85, 90, or 95% identical to SEQ ID NO: 3, or a functional fragment thereof. In some embodiments, methods include introducing into the subject a composition comprising an isolated polypeptide molecule comprising the sequence of SEQ ID NO: 1 with up to about 1, 2, 3, 4, 5, 6, 7, 8, 9, 10, 15, 20, or 25 conservative amino acid substitutions, or a functional fragment thereof. In some embodiments, methods include introducing into the subject a composition comprising an isolated polypeptide molecule comprising the sequence of SEQ ID NO: 3 with up to about 1, 2, 3, 4, 5, 6, 7, 8, 9, 10, 15, 20, or 25 conservative amino acid substitutions, or a functional fragment thereof.

BRIEF DESCRIPTION OF THE SEQUENCE LISTING

SEQ ID NO: 1 is an amino acid sequence for a YadC polypeptide;

SEQ ID NO: 2 is a nucleotide sequence encoding the YadC polypeptide of SEQ ID NO: 1;

SEQ ID NO: 3 is an amino acid sequence for an exemplary fragment of the YadC polypeptide of SEQ ID NO: 1; and

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, compositions, and materials similar or equivalent to those described herein can be used in the practice or testing of the presently-disclosed subject matter, representative methods, compositions, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes compositions and methods for inducing an immune response in a subject. The presently-disclosed subject matter further includes antibodies, such as humanized monoclonal antibodies, that recognize epitopes of YadC, and active antibody fragments. As used herein, the term "immune response" refers to a humoral and/or cellular immune response, in a subject, to an introduction of a composition described herein, which response interferes with or inhibits the virulence, activity, spread, and/or growth of a Yersinia pestis (Y. pestis). Examples of immune responses include the stimulation of antibodies, T-cells, macrophages, B-cells, dendritic cells, etc. These responses can be measured routinely, as will be understood by those of ordinary skill in the art. As used herein, an immune response activity refers to the ability of a compound to elicit an immune response.

As used herein, the term "subject" refers to both human and animal subjects. Thus, veterinary therapeutic uses are provided in accordance with the presently-disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The compositions and methods of the presently-disclosed subject matter can be used for treating a Yersinia pestis (Y. pestis) infection and/or treating a plague resulting from such an infection. As used herein, the terms "treatment" and "treating" relate to any treatment of a Y. pestis, including but not limited to prophylactic treatment (i.e., pre-infection), and therapeutic treatment (i.e., post-infection). The terms "treatment" or "treating" include: preventing the development of a Y. pestis infection and/or plague occurring in a subject; reducing the severity of a Y. pestis infection and/or plague occurring in a subject; and/or ameliorating or relieving the symptoms associated with a Y. pestis infection and/or plague occurring in a subject.

In some embodiments, the compositions and methods of the presently-disclosed subject matter can be used for treating an F1-positive (F1$^+$) or an F1-negative (F1$^-$) Y. pestis strain. In some embodiments, the compositions and methods can be used for treating a Y. pestis CO92 strain. In some embodiments, the compositions and methods can be used for treating an F1$^-$ Y. pestis strain. In some embodiments, the compositions and methods can be used for treating an F1$^-$ Y. pestis CO92 strain. Embodiments of the compositions and methods can be used for treating any Y. pestis strain having a yadC gene.

In some embodiments, compositions include an isolated YadC polypeptide. (YadC is also known as YPO1388 of Y. pestis CO92). In some embodiments, compositions include at least two isolated YadC polypeptides. In some embodiments, compositions can include a YadC polypeptide, and at least one additional compounds for treating Y. pestis infection, for example, one or more of the compounds identified in one of the following references, each of which is incorporated herein by this reference: U.S. Pat. Nos. 3,137,629; 5,985,285; 6,638,510; 6,706,522; and 6,964,770; and U.S. Patent Publication Nos: 2004/0151727; 2005/0136075; 2005/0220797; and 2005/0232940; and PCT Publication Nos: WO95/18231; WO95/24475; WO2004/019980; WO2005/023205; and WO2005/120561.

The terms "polypeptide," "protein," and "peptide" refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. Therefore, the terms "protein," "polypeptide," and "peptide" are used interchangeably herein, unless otherwise noted. Exemplary polypeptides include gene products, naturally occurring proteins, homologs, orthologs, paralogs, fragments and other equivalents, variants, and analogs of the foregoing. The term "isolated", when used in the context of an isolated polypeptide, is a polypeptide that, by the hand of man, exists apart from its native environment and is therefore not a product of nature. An isolated polypeptide can exist in a purified form or can exist in a non-native environment.

As used herein, the term "fragment" refers to a sequence that comprises a subset of another sequence. When used in the context of an amino acid sequence, the terms "fragment" and "subsequence" are used interchangeably. A fragment or subsequence of an amino acid sequence can be any number of residues that is less than that found in a reference polypeptide, and can include, but is not limited to, domains, features, repeats, etc. Also, it is understood that a fragment or subsequence of an amino acid sequence need not comprise the entirety of the amino acid sequence of the domain, feature, repeat, etc. A fragment can also be a "functional fragment," in which the fragment retains some or all of the activity of the reference polypeptide as described herein. For example, a functional fragment of a reference polypeptide that is a Y. pestis antigen can retain some or all of the immune response activity of the reference polypeptide.

The terms "variant" and "modified," when used to describe polypeptide refer to a polypeptide that is different from a reference polypeptide as a result of an intentional manipulation of the amino acid sequence of the polypeptide, or the nucleic acid sequence encoding the amino acid sequence of the polypeptide. For example, a modified polypeptide or polypeptide variant can contain at least one amino acid substitution relative to a reference polypeptide. In some embodiments, a modified polypeptide can include one or more additions and/or deletions or relative to the amino acid sequence of the reference polypeptide, so long as the modified polypeptide maintains some or all of the activity of the reference polypeptide as described herein.

The term "conservatively substituted variant" refers to a polypeptide comprising an amino acid sequence that differs from a reference polypeptide by one or more conservative amino acid substitution, and maintains some or all of the activity of the reference polypeptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes polypeptides wherein a residue is replaced with a chemically derivatized residue, provided that the resulting polypeptide maintains some or all of the activity of the reference polypeptide as described herein.

"Percent identity," or "percent homology" when used herein to describe to an amino acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST) are used.

In some embodiments of the presently-disclosed subject matter, a composition for inducing an immune response in a subject comprises an isolated polypeptide molecule comprising an amino acid sequence encoded by a nucleotide sequence of SEQ ID NO: 2. In some embodiments, the composition for inducing an immune response in a subject comprises an isolated polypeptide molecule comprising an amino acid sequence encoded by a subsequence of the nucleotide sequence of SEQ ID NO: 2, so long as the encoded polypeptide has improved immune response activity relative to, or has all or some of the immune response activity of, a polypeptide encoded by a nucleotide sequence of SEQ ID NO: 2. In some embodiments, the isolated polypeptide molecule comprises an amino acid sequence encoded by a fragment of the nucleotide sequence of SEQ ID NO: 2, wherein up to about 15, 30, 45, 60, 75, 90, 150, 375, or 450 nucleotide residues are truncated from the 5' terminus of SEQ ID NO: 2, and/or up to about 30, 150, 225, 300, 450, 525, 600, 675, 750, 825, 900, 975, 1050, or 1200 nucleotide residues are truncated from the 3' terminus of SEQ ID NO: 2.

In some embodiments, the YadC polypeptide of the compositions includes a polypeptide having an amino acid sequence as set forth in SEQ ID NO: 1, or a functional fragment thereof. For example, in some embodiments, the polypeptide molecule comprises the amino acid sequence including amino acid residues 137-409 of YadC, which fragment is set forth in SEQ ID NO: 3. For another example, in some embodiments, the polypeptide molecule comprises the amino acid sequence including amino acid residues 137-345 of YadC. For another example, in some embodiments, the polypeptide molecule comprises the amino acid sequence including amino acid residues 32-345 of YadC. For another example, in some embodiments, the polypeptide molecule comprises the amino acid sequence including amino acid residues 32-409 of YadC. In some embodiments the polypeptide molecule comprises a fragment of SEQ ID NO: 1, wherein up to about 5, 10, 15, 20, 25, 30, 50, 125, or 150 amino acids are truncated from the N-terminus of SEQ ID NO: 1 and/or wherein up to about 10, 50, 75, 100, 150, 175, 200, 225, 250, 275, 300, 325, 350, or 400 amino acids are truncated from the C-terminus of SEQ ID NO: 1. In some embodiments, the polypeptide molecule comprises at least about 200, 210, 225, 235, 245, 255, 265, 275, 285, 295, 300, 325, 350 or 375 amino acids of SEQ ID NO: 1.

In some embodiments, the YadC polypeptide is a variant, such as a conservatively-substituted variant, of a polypeptide having the amino acid sequence of SEQ ID NO: 1, or a subsequence thereof. For example, in some embodiments, the YadC polypeptide is a conservatively-substituted variant having the amino acid sequence of SEQ ID NO: 1, or a subsequence thereof, with up to about 1, 2, 3, 4, 5, 6, 7, 8, 9, 10, 15, 20, or 25 conservative amino acid substitutions. In some embodiments, the YadC polypeptide is a conservatively-substituted variant of a polypeptide having the amino acid sequence of SEQ ID NO: 3. In some embodiments, up to about 1, 2, 3, 4, or 5 amino acid substitutions are between amino acid residues 32-345 of the YadC polypeptide of SEQ ID NO: 1, or a subsequence thereof. In some embodiments, the amino acid substitutions are primarily between amino acid residues 346-622 of the YadC polypeptide of SEQ ID NO: 1, or a subsequence thereof. In some embodiments, all of the amino acid substitutions are between amino acid residues 346-622 of the YadC polypeptide of SEQ ID NO: 1, or a subsequence thereof. Variants can have improved immune response activity relative to, or can maintain some or all of the immune response activity of the polypeptide having the amino acid sequence of SEQ ID NO: 1.

In some embodiments, the YadC polypeptide is a modified polypeptide, relative to the polypeptide having the amino acid sequence of SEQ ID NO: 1, or a subsequence thereof. Such modified polypeptides can have improved immune response activity relative to, or maintain some or all of the immune response activity of, the polypeptide having the amino acid sequence of SEQ ID NO: 1. In some embodiments, the YadC polypeptide includes a polypeptide having 80%, 85%, 90%, or 95% identity to a polypeptide having the amino acid sequence of SEQ ID NO: 1, or a subsequence thereof, so long as the polypeptide has improved immune response activity relative to, or maintain some or all of the immune response activity of, the polypeptide having the amino acid sequence of SEQ ID NO: 1.

In some embodiments of the presently-disclosed subject matter, the compositions can be provided in a formulation appropriate for administration to a subject, as will be understood by those of ordinary skill in the art. For example, in some embodiments, the compositions can be provided in as a liquid solution or a suspension, suitable for injection. In some embodiments, solid forms of the compositions that are suitable for solution in, or suspension in, liquid prior to injection can be provided. In some embodiments, compositions can be mixed with excipients, such as, for example, water, saline, dextrose, glycerol, ethanol, and combinations thereof. In some embodiments, formulations can include one or more adjuvants. In some embodiments, the adjuvant is a aluminum hydroxide, e.g., aluminum hydroxide gel known as ALHYDROGEL® (E. M. Sergeant Pulp & Chemical Co. (Clifton, N.J.)). Other suitable adjuvants for use in the practice of the present subject matter include, but are not limited to polymers of acrylic or methacrylic acid, maleic anhydride and alkenyl derivative polymers, immunostimulating sequences (ISS), such as oligodeoxyribonucleotide sequences having one or more non-methylated CpG units, cation lipids containing a quaternary ammonium salt, cytokines, and aluminum phosphate.

The presently-disclosed subject matter includes methods for inducing an immune response in a subject, including administering to a subject a composition including a YadC polypeptide, as described above. The composition can be administered in an amount sufficient to induce an immune response in the subject. The presently-disclosed subject matter includes methods for treating a *Yersinia pestis* (*Y. pestis*) infection and/or treating a plague resulting from such an infection, including administering to the subject an effective amount of a composition including a YadC polypeptide, as described above.

As used herein, the term "effective amount" refers to a dosage sufficient to elicit an immune response. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

For additional guidance regarding formulation and dose, see Berkow et al., (1997) *The Merck Manual of Medical Information*, Home ed. Merck Research Laboratories, Whitehouse Station, N.J.; Goodman et al., (2006) *Goodman & Gilman's the Pharmacological Basis of Therapeutics*, 11th ed. McGraw-Hill Health Professions Division, New York; Ebadi, (1998) *CRC Desk Reference of Clinical Pharmacology*. CRC Press, Boca Raton, Fla.; Katzung, (2007) *Basic & Clinical Pharmacology*, 10th ed. Lange Medical Books/McGraw-Hill Medical Pub. Division, New York; Remington et al., (1990) *Remington's Pharmaceutical Sciences*, 18th ed. Mack Pub. Co., Easton, Pa.; and Speight et al., (1997) *Avery's Drug Treatment: A Guide to the Properties, Choice, Therapeutic Use and Economic Value of Drugs in Disease Management*, 4th ed. Adis International, Auckland/Philadelphia.

In some embodiments, compositions can further include additional compounds for treating *Y. pestis* infection, for example, one or more of the compounds identified in one of the following references, each of which is incorporated herein by this reference: U.S. Pat. Nos. 3,137,629; 5,985,285; 6,638,510; 6,706,522; and 6,964,770; and U.S. Patent Publication Nos: 2004/0151727; 2005/0136075; 2005/0220797; and 2005/0232940; and PCT Publication Nos: WO95/18231; WO95/24475; WO2004/019980; WO2005/023205; and WO2005/120561.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Bacterial strains and plasmids. *Y. pestis* CO99-3015 strains were grown in Heart Infusion Broth (Difco laboratories, Detroit, Mich.) supplemented with 2.5 mM $CaCl_2$ and 0.2% xylose (sHIB) on sHIB agar. *E. coli* strains were grown in Luria-Bertani broth (LB) or on LB-based agar. The bacterial strains and plasmids used in studies described herein are set forth in Table 1. Antibiotics were used at the following concentrations during genetic constructions: carbenicillin (Cb), 100 µg/ml; kanamycin, 25 µg/ml chloramphenicol, 25 µg/ml. Cb was used at 50 ug/ml for growth of *Y. pestis* strains containing pCD2Ap. The presence of the pigmentation locus (Perry 1997) was confirmed by the formation of red colonies on Congo Red agar (Surgalla 1969). The presence of a functional Lcr virulence plasmid was confirmed by absence of growth at 37° C. on sHIB agar containing 20 mM $MgCl_2$ and 20 mM sodium oxalate (MgOx plates) and by assaying expression and secretion of Yops during growth in the defined medium TMH (Straley 1986) with and without 2.5 mM $CaCl_2$.

TABLE 1

Bacterial Strains and Plasmids Used in This Study.

| Strain or Plasmid | Key Properties | Source or Reference |
|---|---|---|
| *Y. pestis* | | |
| CO99-3015 | Wildtype strain; subclone of CO92; molecular grouping 1.ORI. | CDC Ft. Collins |
| CO99-3015.S2 | CO92 Pgm⁺ Lcr⁻ Δcaf1, pPst; F1⁻ derivative made by allelic exchange into avirulent Lcr⁻ F1⁺ *Y. pestis* CO99-3015 obtained from Scott Bearden (CDC Ft. Collins); entire caf1 coding sequence and 12 upstream bp deleted. | Spencer Leigh |
| CO99-3015.S5 | CO92 Δpgm Lcr⁺ pFra, pPst; conditionally virulent[a] Δpgm derivative of CO99-3015. | Scott Bearden |
| CO99-3015.S6 | CO92 Δpgm Lcr⁺ pFra, pPst; pCD2 yadA::bla (pCD2Ap; Ap[r]) made from CO99-3015.S5 by allelic exchange; used as source of pCD2Ap for electroporation into Lcr⁻ strains to reconstitute potential virulence. | Forman 2006 |
| CO99-3015.S7 | CO92 Δpgm Lcr⁺ Δcaf1, pPst; F1⁻ Δpgm attenuated strain made from CO99-3015.S5 by allelic exchange. | This Study |
| CO99-3015.S9 | CO92 Pgm⁺ Lcr⁺ Δcaf1, pPst; reconstituted Lcr⁺ F1⁻ conditionally virulent[b] strain made by allelic exchange. | This Study |
| *E. coli* | | |

TABLE 1-continued

Bacterial Strains and Plasmids Used in This Study.

| Strain or Plasmid | Key Properties | Source or Reference |
|---|---|---|
| DH5α | end-1 hsdR17(rk-mk+) supE44 thi-1 recA1 gyrA (Nalr) relA1 Δ(lacIZYA-argF)U169 deoR (Φ80dlacΔ (lacZ)M15). | Life Technologies, Gaithersburg MD |
| | Plasmids | |
| pKD3 | Template plasmid; cat flanked by FRT sites; $Cm^rAp^r$ | Datsenko 2000 |
| pKD46 | Red recombinase expression plasmid; $Ap^r$. | Datsenko 2000 |
| pCP20 | Suicide plasmid with temperature-sensitive replication and thermally induced expression of FLP recombinase; $Ap^rCm^r$ | Datsenko 2000 |
| pHT-V | PCR-amplified lcrV cloned into pProEX-1; expresses full-length LcrV with a $His_6$-containing 23-residue N-terminal leader sequence (HT-LcrV). | Fields 1999 |
| pGEX-$YadC_{137-409}$ | Sequence encoding amino acids 137-409 of YadC in pGEX-3X; expresses GST-$YadC_{137-409}$. | Forman 2006 |

[a]Full virulence is conditional on intravenous route of infection (Perry 1997).
[b]Full virulence is conditional on intranasal route of infection (Davis 1996).

Production of the protein capsule F1 was abolished by deleting the caf1 gene. Primers were used to generate a PCR fragment containing the FRP site-flanked cat gene from pKD3 flanked by caf1 sequence, and caf1 was deleted by allelic exchange mediated by the Red and F1p recombinases as described in Datsenko, 2000. The resulting deletion started at −12 by upstream of the caf1 translation initiation codon through the last translated codon. The absence of F1 expression was verified by immunoblot of 37° C.-grown yersiniae using the monoclonal antibody YPF1 (Research Diagnostics, Inc., Flanders, N.J.), and the absence of cat in the final strain was confirmed by PCR and by inability to grow on chloramphenicol-containing plates.

Virulence was reconstituted in BSL3 containment with select-agent security by introducing pCD2Ap by electroporation. Briefly, *Y. pestis* CO99-3015.S2 was electroporated with plasmid DNA from *Y. pestis* CO99-3015.S6, that contained the *Y. pestis* plasmids pFra (110 kb) and pPst (9 kb) (Perry 1997) in addition to pCD2Ap. Their presence in the transformation would not pose a problem since the recipient strains already contained copies of these two plasmids.

Transformed strains were selected for Cb-resistance and screened for the Pgm+ and Lcr+ phenotypes on agar media. Individual isolates that passed these tests were then subcultured two times in 3 ml TMH+Cb at 26° C. for a total of 24 hours prior to the experiment. The cultures were subcultured a third time into TMH with or without 2.5 mM $CaCl_2$ and allowed to grow for an additional two hours at 26° C. Following this, each culture was shifted to 37° C. and permitted to grow another four hours. A 500-μl sample of each culture was removed and briefly placed on ice to aid cellular aggregation. Cells were pelleted in a microcentrifuge at room temperature (RT) for 10 min. The top 250 μl of supernatant was removed, transferred to a microcentrifuge tube containing trichloroacetic acid to a final concentration of 5%, and incubated overnight at 4° C. to precipitate secreted proteins. The rest of the supernatant was discarded. The precipitated proteins were collected by centrifugation at RT. Pellets of whole cells and of secreted proteins were suspended in lysis loading buffer (400 mM TrisCl, pH 6.8, 25% glycerol, 8% SDS, 5% dithiothreitol, 0.4% bromophenol blue) to a concentration corresponding to a culture $OD_{620}$ of 2.0 and heated to 95° C. for 15 minutes. Half of each heat-treated sample was plated and incubated for 5 days at 28° C. to ensure that no viable cells remained prior to removing the samples from the containment facility.

The resultant cellular extracts and supernatant proteins were then analyzed by immunoblot for the presence of secreted LcrV and YopM, as described in Wulff-Strobel 2001, to determine whether the type three secretion system was fully functional. Several isolated colonies were then pooled and stocked.

Preparation of YadC Polypeptide. The YadC polypeptide selected for testing in the present study was a fragment of the YadC polypeptide of SEQ ID NO: 1. The fragment includes amino acid residues 137-409 of the amino acid sequence of SEQ ID NO:1, which are set forth in SEQ ID NO: 3. To produce GST-$YadC_{137-409}$ (Forman 2006), *E. coli* DH5α containing plasmid pGEX-$YadC_{137-409}$ was grown to an $OD_{620}$ of 0.5, IPTG was added to a final concentration of 1.0 mM and the bacteria were incubated for an additional 3 hours. Cells were harvested by centrifugation at 4° C., and resuspended at 0.05 the original volume in column buffer (20 mM Tris, 200 mM NaCl, 1 mM EDTA pH 7.4). Samples were passed twice through a French press to lyse bacteria, cleared by centrifugation at 9000×g for 30 minutes at 4° C., diluted 1:4 with column buffer and passed over a glutathione sepharose column. Bound protein was eluted using column buffer containing 10 mM glutathione and collected in 1 mL aliquots. Purity was assessed on SDS-PAGE gels stained with Coomasie brilliant blue. Protein-containing fractions were pooled and dialyzed, and the protein concentration measured by the bicinchoninic acid assay (Pierce Chemical Co., Rockford, Ill.).

N-terminally $His_6$-tagged LcrV (HT-LcrV) was expressed in *E. coli* DH5α from plasmid pHT-V and purified on Talon metal-affinity resin (Clonetech Laboratories, Inc, Palo Alto, Calif.) as described by Fields, 1999.

Protection studies. Sets of 5 female outbred Swiss-Webster mice were immunized subcutaneously with 40 μg amounts of purified fusion proteins (GST-$YadC_{137-409}$, or HT-LcrV) or buffer emulsified with ALHYDROGEL® (aluminum hydroxide gel) (Sigma Chemical Company, St. Louis, Mo.; 6.25% vol/vol final concentration) on days 0, 8, 14, and 22. On day 35, they were challenged intravenously with 10,000 CFU (5 LD50 doses) of *Y. pestis* CO99-3015.S7.

Similarly, groups of 8 C57BL/6 mice were immunized with 80 μg of HT-LcrV, GST-$YadC_{137-409}$, or GST (Sigma Chemical Company, St. Louis, Mo.) adjuvanted with ALHYDROGEL® as in the previous experiment. Two weeks after the 3rd immunization, the mice were challenged intranasally with 3000 CFU of CO92.S2 (6 times the LD50 dose) in BSL3 conditions.

Determination of IgG isotypes. Measurement of antibody titer and isotype response was performed by a modified ELISA on serum samples taken 1 week prior to bacterial challenge. 96-well ELISA plates were coated with 10 μg/ml of GST-YadC$_{137-409}$, HT-LcrV, GST or with buffer alone. Mouse sera were then used at serial dilutions to a maximum dilution of 1:5,120,000. HRP conjugates against mouse IgG, IgG1, IgG2a, IgG2b, and IgG3 (BD Pharmingen, San Diego, Calif.) were used as secondary antibodies. Protein-specific antibody titer was estimated as the maximum dilution of serum giving an absorbance at 450 nm reading 0.1 units over the non-immunized mouse background sera (pre-immunization sera). Mean titers were determined per treatment group.

Human macrophages and cytokine analysis. The cytokine response of human peripheral blood monocytes (PBMs) to HT-LcrV, GST-YadC$_{137-409}$, and the negative control GST was evaluated. Blood was obtained from two healthy volunteers. Red blood cells were lysed with ACK buffer (155 mM NH$_4$Cl/l mM KHCO$_3$/0.5 mM EDTA, pH 7.2), the samples were washed, and PBMs were isolated by Ficoll-Paque density gradient. PBMs were cultured for one week in RPMI with 12.5% human serum and 10 μg/ml of penicillin, streptomycin, and neomycin at a concentration of 1×10$^6$ cells/ml in 5% CO$_2$ to differentiate into macrophages.

Differentiated PBMs were stimulated with 10 μg of F1, HT-LcrV, GST, or GST-YadC$_{137-409}$ in 96-well ELISA plates. 100 μL of supernatant was removed at 3 hours and then at 24 hours. Supernatants were kept at −80° C. until processed for cytokine analysis. All analyses were done in triplicate in 2 different experiments. Cytokine levels were measured by Cytokine Bead Analysis (BDBiosciences) and evaluated by flow cytometry.

Results yadC Operon and Predicted Properties of YadC. The adhesin YadA of the enteropathogenic yersiniae is encoded by the same Lcr plasmid that encodes LcrV. YadA contributes to colonization through binding to extracellular matrix components such as fibronectin, collagen, and laminin that in turn are bound to β1 integrins (Tahir E Y 2001; Hudson 2005). YadA belongs to a family of oligomeric coiled-coil (Oca) adhesins that are a subgroup of autotransporters composed of trimers with short outer membrane-anchor domains. The trimeric character may provide increased avidity for tight adherence (Hoiczyk 2000; Cotter 2005). Each YadA monomer is composed of an N-terminal head that contains a collagen binding motif, a neck that serves as a platform for the head and contributes to stability of the complex, a stalk composed of seven 15-mer units, a coiled-coil linker of two to three 7-mer units that is necessary for transport of the head, neck, and stalk through the outer membrane, and a membrane anchor (Hoiczyk 2000; Tahir E Y 2001; Roggenkamp A 2003; Nummelin H 2004).

In *Y. pestis*, the yadA gene contains a frameshift mutation that prevents the expression of a functional YadA protein. To identify surface proteins of potential pathogenic importance for *Y. pestis*, we examined the *Y. pestis* CO92 genome for genes encoding proteins similar to YadA and identified the 1869 by ORF YPO1388 that was subsequently named yadC. yadC is likely part of a bicistronic operon with the upstream 1095 by ORF encoding another protein with homology to YadA and called yadB (YPO1387). yadBC is fairly isolated on the chromosome with the nearest gene upstream gene 300 base pairs away and the nearest downstream gene 366 base pairs away.

The yadB and yadC genes in the chromosome of *Y. pestis* CO92 also encode members of the Oca family (denoted as 653a/b in ref (Hoiczyk 2000)) and share the structural arrangement seen in YadA, although the amino-acid sequence similarity is not strong (FIG. 1). There is essentially no similarity between YadA and the two predicted *Y. pestis* proteins in the head regions. YadC is 25% identical and 45% similar in 285 amino acids in the C-terminus of YadA. yadC encodes a putative 622 amino acid preprotein while yadB encodes a putative 364 residue preprotein. The predicted YadC protein (61.6 kDa) has a much larger head domain than does YadB (35 kDa), which carries only a short extension N-terminal to the neck domain. The isoelectric point of YadC is 4.0 while YadB's PI is 4.5. Both YadB and YadC have signal sequences as found by SignalP 3.0 (Bendtsen 2004). These observations, considered with the yadBC bicistronic genetic arrangement, suggest that YadB and YadC may function together.

Importance of YadC for virulence in bubonic plague. Applicants have found that some human plague convalescent sera recognize YadC, and a yadBC mutant *Y. pestis* has been found to show decreased adherence to epithelioid cells (Forman 2006), suggesting that YadB and YadC might have a virulence role in plague. Further, the yadBC mutant was attenuated from the subcutaneous route (mimicking bubonic plague) as compared to the virulent *Y. pestis* parent strain. This finding shows that yadBC encodes a new virulence determinant for bubonic plague. This attenuation was not demonstrated when mice were challenged intranasally (mimicking pneumonic plague).

Protection studies. One goal of the studies described herein is to obtain information useful for improving subunit plague treatment by identifying components that will provide protection against pneumonic plague due to an $F1^-$ *Y. pestis* strain or against bubonic and systemic plague due to an $F1^+$ strain. Since YadC was determined to be a virulence factor for bubonic plague and is detectable by antibody. it likely is displayed on the bacterial surface where it would be accessible to antibody. Therefore, its role as a protective antigen was tested. Two tests were made for protective efficacy, using different challenge strains and infection routes. Mice were immunized and challenged either intravenously or intranasally, as outlined above.

Negative-control mice received either ALHYDROGEL® only or GST-ALHYDROGEL® immunization. HT-LcrV-immunized mice were used as the positive control. From an intravenous route, a test with Swiss-Webster mice challenged with 5 $LD_{50}$ doses (10,000 CFU) of *Y. pestis* CO99-3015.S7 revealed no protection for those immunized with buffer alone, full protection for HT-LcrV-immunized mice, and partial protection for GST-YadC$_{137-409}$-immunized mice (with 40% of mice surviving) (FIG. 2). After intranasal challenge, 87% of GST-YadC$_{137-409}$ C57BL/6 mice given 6 $LD_{50}$ doses (3,000 CFU) of *Y. pestis* CO99-3015.S9 survived pneumonic plague. This is compared to the GST control group (0 surviving mice) and the HT-LcrV-immunized group where 50% survived the challenge (FIG. 3). There was not a significant difference in survival between mice immunized with GST-YadC$_{137-409}$ or with HT-LcrV in either experiment; however, there was a significant difference between results for both proteins when compared to the GST- or ALHYDROGEL®-only negative control groups. Accordingly, YadC appears to be protective against $F1^-$ *Y. pestis* from both intravenous and intranasal routes. This test also supports the prediction that YadC is accessible to antibody in vivo and is a true surface-localized protein.

IgG isotypes. Protein-specific IgG1, IgG2A, and IgG2B, and IgG3 antibodies were measured by ELISA in the sera of the mice immunized with GST-ALHYDROGEL®, GST-YadC$_{137-409}$ or HT-LcrV. As has been reported, protection with the F1-LcrV antigen is associated with predominantly a Th2 IgG1 response (Williamson 1999). Likewise, in experiments described herein, mice immunized with HT-LcrV demonstrated a similar IgG isotype distribution (IgG1>IgG2a~IgG2b~IgG3, p<0.005 when IgG1 compared to other isotypes). Mice immunized with YadC demonstrated a more balanced Th1/Th2 response (IgG1=IgG3>IgG2a>IgG2b, p<0.005 when IgG1 and IgG3 compared to other isotypes). The total IgG titers to GST-YadC$_{137\text{-}409}$ ($1:5.6\times10^6$) were significantly higher than those for HT-LcrV ($1:1\times10^6$) and total IgG titers to the GST component in the negative control mice ($1:6.4\times10^5$).

Figure 1:
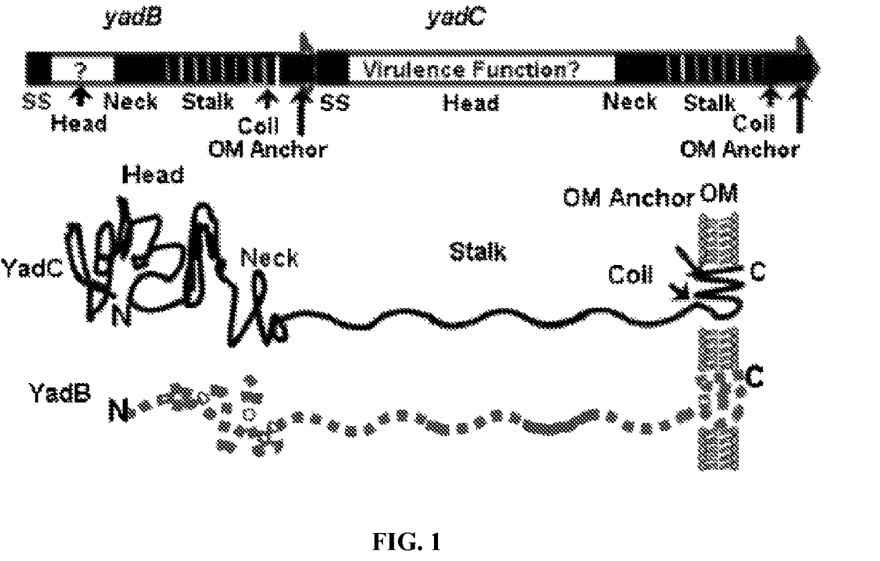
FIG. 1 is a schematic representation of the predicted structure of YadB and YadC.
Figure 2:
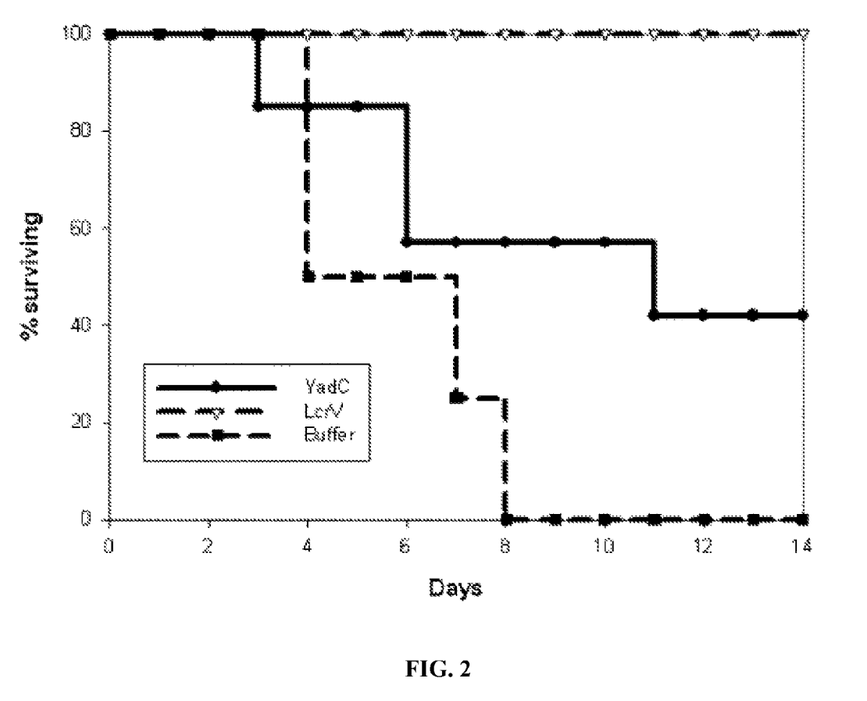
FIG. 2 is a graph depicting the results of a study wherein immunized mice were intravenously challenged with *Y. pestis*. There was no protection for those immunized with buffer alone (Buffer), full protection for HT-LcrV-immunized mice (LcrV), and partial protection for GST-YadC$_{137-409}$-immunized mice (YadC).
Figure 3:
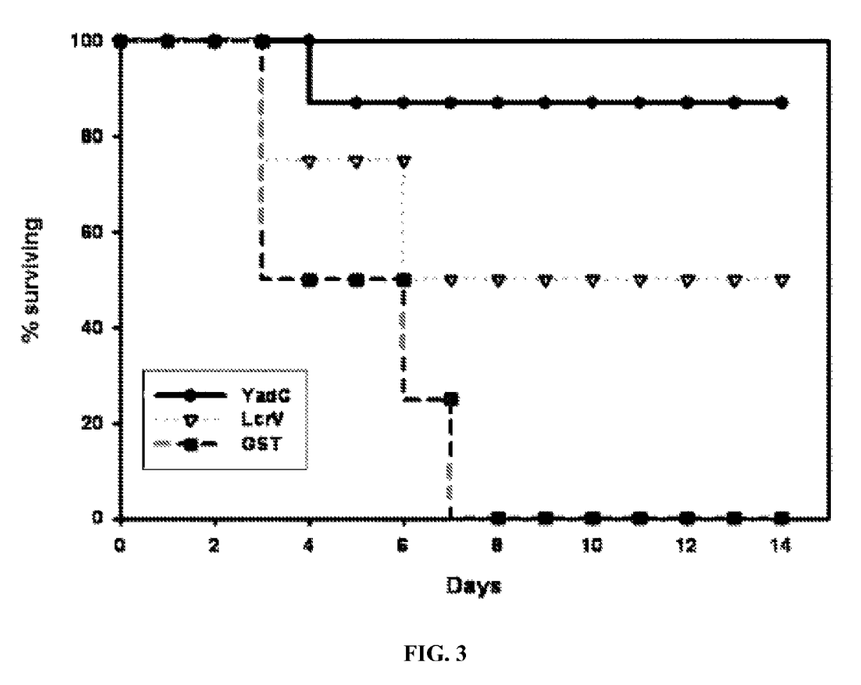
FIG. 3 is a graph depicting the results of a study wherein immunized mice were intranasally challenged with *Y. pestis*. 87% of GST-YadC$_{137-409}$-immunized mice survived pneumonic plague, as compared to the GST-immunized control group (0 surviving mice) and the HT-LcrV-immunized group, where 50% survived.
Figure 4A:
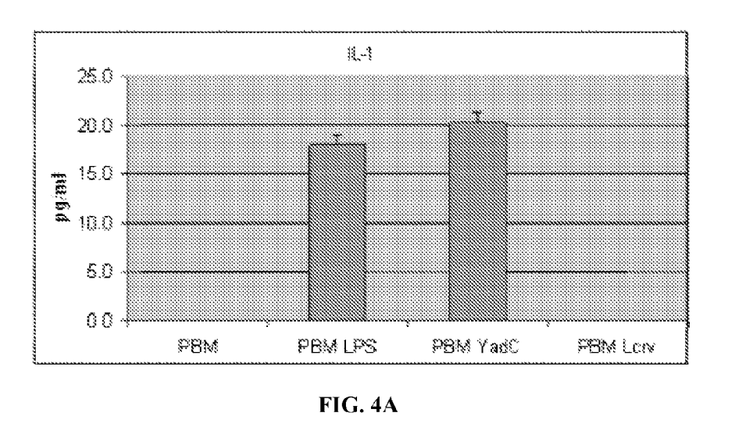
FIGS. 4A-4D are a series of bar graphs depicting peripheral macrophage (PBM) cytokine response. GST-YadC$_{137-409}$ leads to increased IL-1, IL-6 and TNF-α production when compared to HT-LcrV.
Figure 4B:
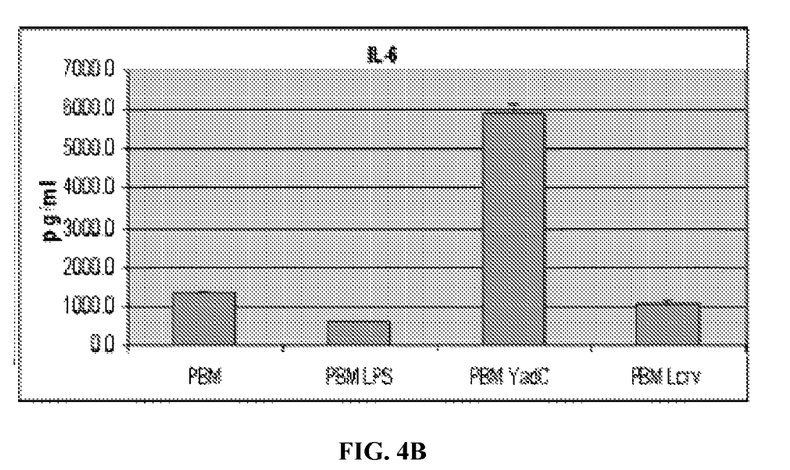
Figure 4C:
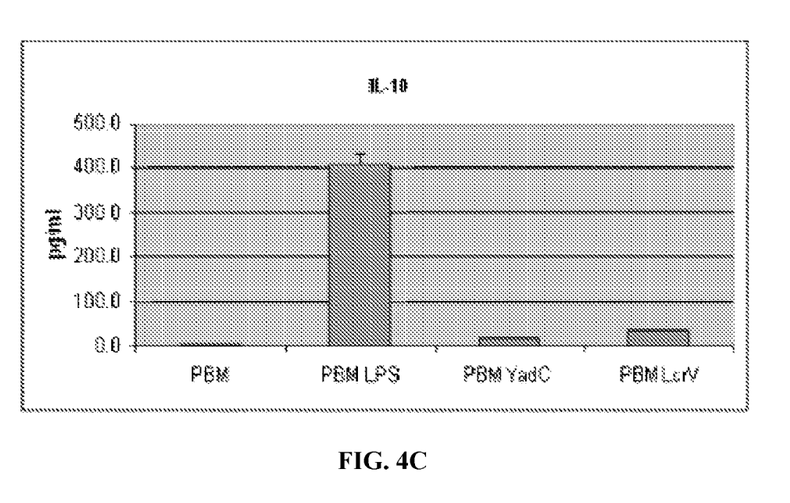
Figure 4D:
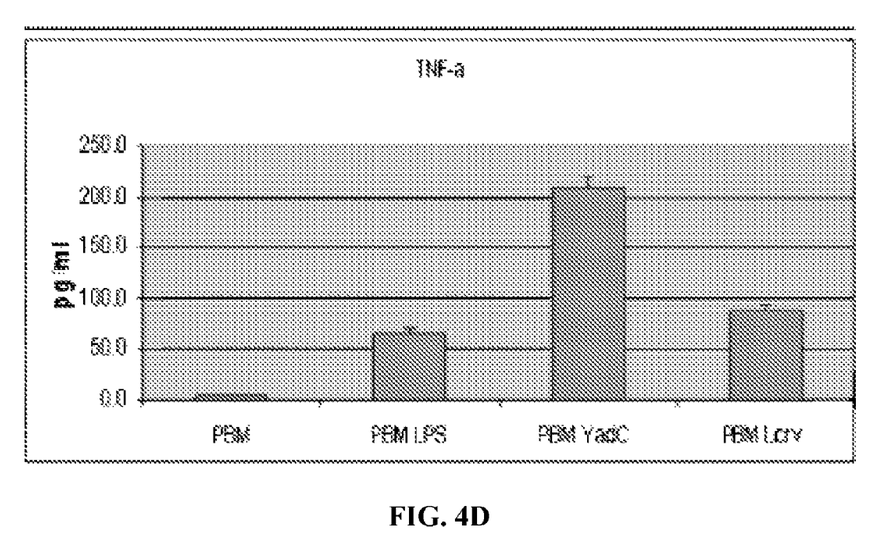

Anti-inflammatory/pro-inflammatory cytokines. In response to stimulation with either GST-YadC$_{137\text{-}409}$, HT-LcrV, or GST, PBMs produced little or no IL-10. PBMs stimulated with YadC showed a significant TNF-α and IL-6 production that was much higher than that due to LPS or HT-LcrV (FIG. 4). IL-12 production was not detectable in response to either GST-YadC$_{137\text{-}409}$ or HT-LcrV (not shown) but a small amount of IL-1 was produced in response to GST-YadC$_{137\text{-}409}$ but not to HT-LcrV. Overall, YadC provided more of a pro-inflammatory response than did LcrV (i.e., increased IL-1 and IL-6). This finding suggests that a more balanced Th1/Th2 plague treatment composition is possible. An experiment was also conducted using human alveolar macrophages (AM) from bronchoalveolar lavage fluid. This test revealed a different cytokine profile with significantly more IL-10 produced in response to HT-LcrV than to GST-YadC$_{137\text{-}409}$ and significant IL-12 production after stimulation with GST-YadC$_{137\text{-}409}$ but not with HT-LcrV or GST alone (data not shown). Again, the overall picture was that GST-YadC$_{137\text{-}409}$ was more pro-inflammatory and HT-LcrV was anti-inflammatory. These different cytokine profiles suggest that the antigens presented during bubonic and pneumonic plague have a very different immune effect. These data, combined with the previous challenge experiments, provide evidence that surface proteins like YadC would be beneficial in inducing a more robust adaptive immunity response in future plague treatment compositions.

Discussion. It is clear from previous studies (Cowan 2000) that *Y. pestis* has multiple adhesins and invasins to substitute for the absence of proteins such as YadA. These and other *Y. pestis* surface proteins could alter the current plague treatment compositions to elicit a more balanced Th1/Th2 phenotypic profile. Antigens, such as those identified herein, are desirable for their ability to induce production of antibodies that can block crucial surface function such as epithelial adhesion and invasion. Ideally, genes for such crucial proteins could not be deleted from a potential bioterroristic weapon without loss of virulence, unlike F1. This study examined *Y. pestis* YadC which, as an acidic protein, could have a significant impact on the bacterial surface and be important in host-pathogen interactions.

A critical step in the clearance of pulmonary infections is the ability of the lung antigen-presenting cell to migrate to regional lymph nodes where it can present the antigen to T cells to initiate an adaptive immune response. Previous studies have demonstrated a role for macrophage-lineage cells in mediating protection by anti-LcrV antibody in at least the liver (Philipovskiy A V 2004; Cowan C 2005; Philipovskiy 2005). Recently it has been shown that when Lcr$^-$ *Y. pestis* was given to mice intratracheally, the bacteria were taken up by a characteristic population of DCs (CD11c$^+$DEC205$^{30}$ CD11b$^-$) (Bosio C 2005). Data presented here suggest that PBMs when stimulated by a more favorable antigen (i.e., YadC) can participate in the induction of cytokines such as IL-1, TNF-α, and IL-6 that would favor development of adaptive Th1 cellular immunity in the lung and increased local inflammatory response. Additional pro-inflammatory cytokines from AMs suggest that YadC may play a role in recruiting additional innate immune cells such as natural killer cells to the lung environment.

Finally, as YadC has shown to be required for virulence from a subcutaneous infection and is partially protective against pneumonic and systemic plague, it is believed that YadC polypeptides can be included in useful compositions for treating *Y. Pestis* infection.

F1$^+$ Subcutaneous Challenge and F1$^-$ Intranasal Challenge of Subjects Treated with Composition Including Full-Length YadC Polypeptide.

The following is a prophetic example. Studies are conducted to determine whether subjects treated with a composition including the YadC polypeptide of SEQ ID NO: 1 are protected from: subcutaneous challenge with *Y. Pestis* CO92 pCD2 Ap(res) F1$^+$, and intranasal challenge with *Y. Pestis* CO92 pCD2 Ap(res) F1$^-$.

For the study involving subcutaneous challenge, three groups of mice are provided. A test group is immunized with the composition including the YadC polypeptide of SEQ ID NO: 1, a positive control group is immunized with an HT-LcrV composition, and a negative control group receives adjuvant alone (ALHYDROGEL®). *Y. Pestis* CO99 F1$^+$ cells are plated on HIB agar plates containing 2.5 mM CaCl$_2$, 0.10% xylose containing 50 μg/ml Cb (sHIB$_{Cb50}$ agar), and Congo Red containing 50 μg/ml Cb (Congo Red$_{cb50}$). Pigmentation (Pgm+) colonies are picked and placed into media. The sample is then vortexed and the concentration is determined by obtaining the OD$_{620}$ of a 1:20 dilution. Mice are anesthetized, and subcutaneously challenged with about 100 cells/100 μl of CO99 F1$^+$ *Y. pestis*.

For the study involving intranasal challenge, three groups of mice are provided. A test group is immunized with the composition including the YadC polypeptide of SEQ ID NO: 1, a positive control group is immunized with an HT-LcrV composition, and a negative control group receives adjuvant alone (ALHYDROGEL®). *Y. Pestis* CO99 F1$^+$ cells are plated on HIB agar plates containing 2.5 mM CaCl$_2$, 0.10% xylose containing 50 μg/ml Cb (sHIB$_{cb50}$ agar), and Congo Red containing 50 μg/ml Cb (Congo Red$_{cb50}$). Pigmentation (Pgm+) colonies are picked and placed into media. The sample is then vortexed and the concentration is determined by obtaining the OD$_{620}$ of a 1:20 dilution. Mice are anesthetized, and intranasally challenged with about 5000 cells/20 μl of CO99 F1$^-$ *Y. pestis*.

For the HT-LcrV-treated mice receiving subcutaneous challenge, no symptoms are observed, and there is an overall survival of 100%. For the mice treated with adjuvant alone, after subcutaneous challenge, there is a low overall survival. For YadC (SEQ ID NO:1)-treated mice receiving subcutaneous challenge with CO99 F1$^+$ *Y. pestis*, there is a protective effect, as compared to the mice receiving adjuvant alone.

For the HT-LcrV-treated mice receiving intranasal challenge with CO99 F1$^-$ *Y. pestis*, no symptoms are observed, and there is an overall survival of 100%. For the mice treated with adjuvant alone, after intranasal challenge, there are no mice that survive. For YadC (SEQ ID NO:1)-treated mice receiving intranasal challenge with CO99 F1$^-$ *Y. pestis*, there is a protective effect, as compared to the mice receiving adjuvant alone.

Throughout this document, various references are mentioned. All such references are incorporated herein by reference, including the references set forth in the following list:

Anderson G W., Jr., P L Worsham, C R Bolt, G P Andrews, S L Welkos, A M Friedlander, and J P Burans (1997). Protection of mice from fatal bubonic and pneumonic plague by passive immunization with monoclonal antibodies against the F1 protein of *Yersinia pestis*. *Am J Trop Med Hyg* 56: 571-573.

Andrews, G, D G Heath, G W Anderson, Jr., S L Welkos, and A M Friedlander. (1996). Fraction 1 capsular antigen (F1) purification from *Yersinia pestis* CO92 and from an *Escherichia coli* recombinant strain and efficacy against lethal plague challenge. *Infec. Immun* 64: 2180-2187.

Bendtsen, J D, H Nielsen, G von Heijne and S Brunak. 2004. Improved detection of signal peptides: SignalP 3.0. *J. Mol. Biol.* 340: 783-795.

Bosio C, A W Goodyear., and S W Dow (2005). Early interaction of *Yersinia pestis* with APCs in the lung. *J Immunol* 175: 6750-6756.

British and US vaccine research groups. (2002). Abstracts O-35 and O-40, 8th International Symposium on *Yersinia* September 2002. Turky, Finland.

Cotter, S., N K Surana, and J W St. Geme III (2005). Trimeric autotransporters: a distinct subfamily of autotransporter proteins. *Trends Microbiol* 13: 199-205.

Cowan C, A V Philipovskiy, C R Wulff-Strobel, Z Ye, and S C Straley (2005). Anti-LcrV antibody inhibits delivery of Yops by *Yersinia pestis* KIM5 by directly promoting phagocytosis. *Infect Immun* 73: 6127-6137.

Cowan, C, H A Jones, Y H Kaya, R D Perry, and S C Straley (2000). Invasion of epithelial cells by *Yersinia pestis*: evidence for a *Y. pestis*-specific invasin. *Infect Immun* 68(8): 4523-4530.

Datsenko, K A, and B L Wanner. 2000. One-step inactivation of chromosomal genes in *Escherichia coli* K-12 using PCR products. *Proc. Natl. Acad. Sci. USA* 97: 6640-6645.

Davis, K, D L Fritz, M L M Pitt, S L Welkos, P L Worsham, and A M Friedlander. (1996). Pathology of experimental pneumonic plague produced by fraction 1-positive and fraction 1-negative *Yersinia pestis* in African green monkeys (*Cercopithecus aethiops*). *Arch Pathol Lab Med* 120: 156-163.

DeBord, K, D M Anderson, M M Marketon, K A Overheim, R W DePaolo, N A Ciletti, B Jabri, and O Schneewind (2006). Immunogenicity and protective immunity against bubonic plague and pneumonic plague by immunization of mice with the recombinant V10 antigen, a variant of LcrV. *Infect Immun* 74(8): 4910-4914.

Eyles, J, I D Spiers, E D Williamson, and H O Alpar (1998). Analysis of local and systemic immunological responses after intra-tracheal, intra-nasal and intra-muscular administration of microsphere co-encapsulated *Yersinia pestis* sub-unit vaccines. *Vaccine* 16: 2000-2009.

Eyles, J, S J Elvin, A Westwood, C S LeButt, H O Alpar, S Somavarapu, and E D Williamson. (2004). Immunisation against plague by transcutaneous and intradermal application of subunit antigens. *Vaccine* 22: 4365-4373.

Fields, K A, and S C Straley. 1999. LcrV of *Yersinia pestis* enters infected eukaryotic cells by a virulence plasmid-independent mechanism. *Infect. Immun.* 67:4801-4813.

Forman, S., C R Wulff, R D Perry and S C Straley (2006). Manuscript in preparation.

Friedlander, A, SL Welkos, P L Worsham, G P Andrews, D G Heath, G W Anderson, Jr., L M Pitt, Estep, and K Davis. (1995). The relationship between virulence and immunity as revealed in recent studies of the F1 capsule of *Yersinia pestis Clin. Infect. Dis.* 21: S178-S181.

Glynn, A, C J Roy, B S Powell, J J Adamovicz, L C Freytag, and J D Clements. (2005). Protection against aerosolized *Yersinia pestis* challenge following homologous and heterologous prime-boost with recombinant plague antigens. *Infect Immun* 73(8): 5256-5261.

Glynn, A, L C Freytag, and J D Clements (2005). Effect of homologous and heterologous prime-boost on the immune response to recombinant plague antigens. *Vaccine* 23: 1957-1965.

Gruchalla, R S, and J. Jones. (2003). Combating high-priority biological agents: what to do with drug-allergic patients and those for whom vaccination is contraindicated? *J Allergy Clin Immunol* 112: 675-682.

Heath, D, G W Anderson, Jr., J M Mauro, S L Welkos, G P Andrews, J Adamovicz, and A M Friedlander (1998). Protection against experimental bubonic and pneumonic plague by a recombinant capsular F1-V antigen fusion protein vaccine. *Vaccine* 16: 1131-1137.

Hoiczyk, E, A Roggenkamp, M Reichenbecher, A Lupas, and J Heeseman (2000). Structure and sequence analysis of *Yersinia* YadA and *Moraxella* UspAs reveal a novel class of adhesins. *EBMO J* 19: 5989-5999.

Hudson, K., J B Bliska, and A H Bouton (2005). Distinct mechanisms of integrin bindings by *Yersinia pseudotuberculosis* adhesins determine the phagocytic response of host macrophages. *Cell Microbiol* 7: 1471-1489.

Inglesby T V, D T Dennis, D A Henderson, J G Bartlett, M S Ascher, E Eitzen, A D Fine, A M Friedlander, J Hauer, J F Koerner, et al (2000). Plague as a biological weapon: Medical and public health management. Working Group on Civilian Biodefense. *J Am Med Assoc* 283: 2281-2290.

Lahteenmaki, K, M Kukonen, and T K Korhonen (2001). The Pla surface protease/adhesin of *Yersinia pestis* mediates bacterial invasion into human endothelial cells. *FEBS Lett* 504: 69-72.

Leary, S, K F Griffin, H S Garmory, E D Williamson, and R W Titball (1997). Expression of an F1/V fusion protein in attenuated *Salmonella typhimurium* and protection of mice against plague. *Microb Pathog* 23: 167-179.

Marshall J D, Jr., P J Bartelloni, D C Cavanaugh, P J Kadull, and K F Meyer (1974). Plague immunization. II. relation of adverse clinical reactions to multiple immunizations with killed vaccine. *J Infect Dis* 129 (Suppl): S19-S25.

Motin, V., R Nakajima, G B Smirnov, and R R Brubaker (1994). Passive immunity to yersiniae mediated by anti-recombinant V antigen and protein A-V antigen fusion peptide. Infect Immun 62: 4192-4201.

Nakajima, R, V L Motin, and R R Brubaker (1995). Suppression of cytokines in mice by protein A-V antigen fusion peptide and restoration of synthesis of active immunization. *Infect Immun* 63: 3021-3029.

Nakajima, R, and R R Burbaker. (1993). Association between virulence of *Yersinia pestis* and suppression of gamma interferon and tumor necrosis factor alpha. *Infect Immun* 61: 23-31.

Nedialkov, Y, V L Motin, and R R Brubaker (1997). Resistance to lipopolysaccharide mediated by the *Yersinia pestis* V antigen-polyhisitidine fusion peptide: amplification of interluekin-10. *Infect Immun* 65: 1196-1203.

Nummelin H, M C Merckel, J C Leo, H Lankinen, M Skurnik, and A Goldman (2004). The *Yersinia* adhesin YadA collagen-binding domain structure is a novel left-handed parallel beta-roll. *EBMO J* 23: 701-711.

Perry, R, and J D Fetherston (1997). *Yersinia pestis*—etiologic agent of plague. *Clin Microbiol Rev* 10(1): 35-66.

Philipovskiy, A V, C Cowan, C R Wulff-Strobel, S H Burnett, E J Kerschen, D A Cohen, A M Kaplan, and S C Straley (2005). Antibody against V antigen prevents Yop-dependent growth of *Yersinia pestis*. *Infect Immun* 83 (1532-1542).

Philipovskiy A V, C Cowan, C R Wulff-Strobel, S H Burnett, E J Kerschen, D A Cohen, A M Kaplan, and S C Straley (2004). Antibody against V antigen prevents Yop-dependent growth of *Yersinia pestis*. *Infect Immun* 83 (1532-1542).

Roggenkamp A, N A Ackerman, C A Joacobi, K Truelzsch, H Hoffman, and J Heeseman (2003). Molecular analysis of transport and oligomerization of the *Yersinia enterocolitica* adhensin YadA. *J Bacteriol* 185: 3735-3744.

Russell, P, S M Eley, S E Hibbs, R J Manchee, A J Stagg, and R W Titball (1995). A comparison of plague vaccine, USP and EV76 vaccine induced protection against *Yersinia pestis* in a murine model. *Vaccine* 13: 1551-1556.

Simpson, W, R E Thomas, and T G Schwan. (1990). Recombinant capsular antigen (fraction 1) from *Yersinia pestis* induces a protective antibody response in BALB/c mice. *Am J Trop Med Hyg* 43: 389-396.

Sing, A, A Roggenkamp, A M Geiger, and J. Heesemann. (2002). *Yersinia enterocolitica* evasion of the host immune response by V antigen-induced IL-10 production of macrophages is abrogated in IL-10-deficient mice. *J Immunol* 168: 1315-1321.

Sing, A, N Tvardovaskaia, D Rost, C Kirschning, H Wagner, and J. Heesemann. (2003). Contribution of Toll-like receptors 2 and 4 in an oral *Yersinia enterocolitica* mouse infection model. *Int J Med Microbiol* 293: 341-348.

Sing, A, Tvardovskaia N, Rost D, Kirschning C J, Wagner H, and J Heeseman (2003). *Yersinia* V-antigen exploits toll-like receptor 2 and CD14 for interleukin 10-mediated immunosuppression. *J Exp Med* 197: 1017-1024.

Straley, S C, and W S Bowmer (1986). Virulence genes regulated at the transcriptional level by $Ca^{2-}$ in *Yersinia pestis* include structural genes for outer membrane proteins. *Infect Immun* 51: 445-454.

Surgalla, M, and E D Beesley (1969). Congo red-agar plating medium for detecting pigmentation in *Pasturella pestis*. *Appl Microbiol* 18: 834-837.

Tahir E Y, and M Skurnik. (2001). YadA, the multifaceted *Yersinia* adhesin. *Int J Med Microbiol* 291: 209-218.

Welkos, S, K M Davis, L M Pitt, P L Worsham, and A M Friedlander. (1995). Studies on the contribution of the F1 capsule-associated plasmid pFra to the virulence of *Yersinia pestis*. *Contrib. Microbiol. Immunol.* 13: 299-305.

Williamson, E, H C Flick-Smith, C LeButt, C A Rowland, S M Jones, E L Waters, R J Gwyther, J Miller, P J Packer, and M Irving. (2005). Human Immune Response to a Plague Vaccine Comprising Recombinant F1 and V Antigens *Infection and Immunity* 2005: 3598-3608.

Williamson, E, P M Vessey, K J Gillhespy, S M Eley, M Green, and R W Titball (1999). An IgG1 titre to the F1 and V antigens correlates with protection against plague in the mouse model. *Clin Exp Immunol* 116: 107-114.

Williamson, E, S M Eley, A J Stagg, M Green, P Russell, and R W Titball. (1997). A sub-unit vaccine elicits IgG in serum, spleen cell cultures and bronchial washings and protects immunized animals against pneumonic plague. *Vaccine* 15: 1079-1084.

Wulff-Strobel, C. R., A. W. Williams, and S. C. Straley. 2001. LcrQ and SycH function together at the Ysc type III secretion system in *Yersinia pestis* to impose a hierarchy of secretion. Mol. Microbiol. 43: 411-423.

Murphy, B. S., C. R. Wulff, B. A. Garvy, and S. C. Straley. *Yersinia pestis* YadC: A Novel Vaccine Candidate Against Plague, The Genus *Yersinia*, v. 603, p. 400-414, Springer New York, (In Press).

---

What is claimed is:

1. A composition for inducing an immune response in a subject, comprising a fusion protein including GST and amino acid residues 137-409 of YadC (SEQ ID NO: 3).

2. The composition of claim 1, wherein the composition induces an immune response against F1-positive and F1-negative strains of *Y. pestis*.

3. The composition of claim 1, wherein the composition induces an immune response against F1-negative strains of *Y. pestis*.

4. A method of inducing an immune response in a subject, comprising: introducing into the subject a composition of claim 1.

5. The method of claim 4, wherein the composition induces an immune response against F1-positive and F1-negative strains of *Y. pestis*.

6. The method of claim 4, wherein the composition induces an immune response against F1-negative strains of *Y. pestis*.

7. The method of claim 4, wherein the subject is in need of treatment for a *Y. pestis* infection.

8. The method of claim 4, wherein the subject is susceptible to *Y. pestis* infection.

9. A composition for inducing an immune response in a subject, comprising: a fusion protein comprising: a fragment of the YadC polypeptide consisting of amino acid residues 137-409 of YadC (SEQ ID NO: 3); and additional amino acids at the N-terminal and/or C-terminal end of the fragment (SEQ ID NO: 3) that differ from those amino acids present in the YadC polypeptide (SEQ ID NO: 1).

10. A composition for inducing an immune response in a subject, comprising: an isolated polypeptide molecule consisting of amino acid residues 137-409 of YadC (SEQ ID NO: 3).

* * * * *

SEQUENCE LISTING

<160> NUMBER OF SEQ ID NOS: 3

<210> SEQ ID NO 1
<211> LENGTH: 622
<212> TYPE: PRT
<213> ORGANISM: Yersinia pestis

<400> SEQUENCE: 1

```
Met Asn Lys Glu Ile Lys Arg Met Gln Arg Met Gln Cys Ile Tyr Ile
1               5                   10                  15

Ala Thr Trp Leu Ile Ala Val Phe Thr Ser Pro Ile Val Ile Ala Asn
            20                  25                  30

Asn Thr Asn Ile Asn Gly Ser Thr Asn Asn Gly Asn Gly Thr Ile
        35                  40                  45

Asn Ile Phe Asp Ala Ser Ser Asn Asn Asp Ile His Thr Leu Thr Gly
    50                  55                  60

Leu Gly Asn Glu Gln Leu Gly Gly Phe Ser Asn His Leu Ile Asp Ser
65                  70                  75                  80

His Asn Asn Thr Ile Asp Gly Gly Gln Ser Asn Asn Leu Val Ser Ser
            85                  90                  95

Asp Gly Asn Met Ile Ser Ala Ile Ser Leu Gly Asp Gly Leu Phe Tyr
            100                 105                 110

Gly Ala Gln Asn Asn Thr Leu Ile Asn Ser Asn Asn Asn Leu Leu Ile
        115                 120                 125

Val Thr Gln Gly Ser Thr Ile Ile Asp Ser Asp Ser Asn Thr Val Ser
    130                 135                 140
```

```
Gly Ile Ser Asn Asn Leu Ile Glu Ser Asn Ser Asn Ile Ile Gly Asn
145                 150                 155                 160

Glu Asn Ser Cys Tyr Ser Asp Pro Ala Ser Pro Ser Gly Ala Trp Cys
            165                 170                 175

Val Asp Asn Gln Asn Thr Leu Ile Gly Ser Asp Asn Asn Thr Ile Thr
        180                 185                 190

Gly Ala Leu Asn Gly Leu His Asn Ser His Asn Asn Asp Ile Ile Ala
    195                 200                 205

Ser Ser Val Asn Asn Leu Met Asp Thr His Asn Asn Ile Ile Ala Gly
210                 215                 220

Gly His Tyr Asn Thr Ile Ser Gly Gly Asn Asn Asp Ile Phe Gly
225                 230                 235                 240

Ser Glu Asn Asn Val Thr Asp Ser Thr Asp Ala Asn Ile Asn Gly Ser
            245                 250                 255

Asn Asn Tyr Val Ile Asp Gly Asn Gly Ile Gly Arg Asp Asp Leu Thr
        260                 265                 270

Glu Asp Asn Ser Ile Leu Gly Gly Ser Gly Asn Met Gly Val Gly Asp
    275                 280                 285

Ser Val Thr Ala Ile Thr Asn Ser Val Val Phe Gly Gly Asn Thr Ser
290                 295                 300

Gly Asn Ser Thr Gly Ser Thr Leu Thr Asp Ser Val Ser Val Ser Gly
305                 310                 315                 320

Asn Gly Thr Ser Gly Asn Asn Val Val Asn Ile Gly Gly Ala Ala Asn
            325                 330                 335

Gly Asn Asn Ser Ala Ser Leu Gly Thr Gly Ser Val Ser Ser Glu Gly
        340                 345                 350

Gly Ile Ala Leu Gly Ser Gly Ser Ile Ala Thr Arg Asn Asp Glu Leu
    355                 360                 365

Asn Ile Gly Asp Arg Gln Ile Thr Ser Val Lys Lys Gly Val Glu Asn
370                 375                 380

Thr Asp Thr Ile Asn Val Ser Gln Leu Asn Asp Ser Phe Asp Val
385                 390                 395                 400

Leu Asn Leu Ser Asn Glu Tyr Ser Asp Asn Ser Phe Ser Thr Val Thr
            405                 410                 415

Glu Asn Ile Asn Asn Tyr Thr Asp Ala Ser Leu Asp Thr Val Leu Asn
        420                 425                 430

Thr Thr Gly Glu Tyr Thr Asp Asn Ser Ile Leu Val Thr Asn Glu
    435                 440                 445

Ser Asn Asn Tyr Thr Asp Asn Gly Met Glu Ser Val Ser Asn Tyr Ala
450                 455                 460

Asn Ile Tyr Ala Asp Glu Ser Leu Leu Ala Ile Tyr Asn Glu Glu Ala
465                 470                 475                 480

Asn Tyr Met Ser Asn Leu Ile Asp Val Thr Leu Asn Asn Ala Asn Asn
            485                 490                 495

Tyr Thr Asp Leu Ser Val Asn Thr Ile Ile Tyr Thr Gly Lys Gln Tyr
        500                 505                 510

Thr Asp Ser Arg Ile Asn Glu Tyr Gln Arg Thr Phe Lys Asn Glu Phe
    515                 520                 525

Leu Thr Tyr Ser Asn Gly Lys Phe Gly Gly Phe Asp Lys Asp Ile Asn
530                 535                 540

Gln Lys Gln Lys Gln Leu Asn Ala Gly Ile Ala Ala Thr Met Ala Ala
545                 550                 555                 560
```

```
Ala Val Ile Pro Gln Lys Ser Gly Ser Lys Val Ser Ile Gly Val Gly
                565                 570                 575

Leu Ala Gly Tyr Ser Asp Gln Gly Ala Gly Ser Val Gly Ala Ile Trp
            580                 585                 590

His Val Asn Gln Arg Ile Thr Met Asn Thr Thr Met Thr Tyr Asp Thr
        595                 600                 605

Gln Arg Gly Val Ser Leu Leu Thr Gly Leu Ser Ile Gly Ile
    610                 615                 620

<210> SEQ ID NO 2
<211> LENGTH: 1869
<212> TYPE: DNA
<213> ORGANISM: Yersinia pestis

<400> SEQUENCE: 2
```

| | |
|---|---:|
| atgaataagg aaattaaacg gatgcaacgg atgcaatgca tatatatcgc cacttggtta | 60 |
| atcgcagtat ttacttcgcc gatagtgata gctaacaata cgaatattaa tggcagtacc | 120 |
| aataataacg gtaatggtac aatcaatatt tttgacgcca gcagtaataa cgatattcat | 180 |
| acactaaccg gtcttggtaa tgagcagttg gaggattta gtaatcatct tatcgactct | 240 |
| cataataata cgatagacgg tggtcagagt aacaacctgg taagtagcga tggcaatatg | 300 |
| atcagcgcca ttagcttggg cgatggcctc ttctacggcg cgcagaataa cacgttaata | 360 |
| aactcaaaca acaacctact tattgtcact cagggcagta ctataataga ttctgatagt | 420 |
| aatactgtgt ctggcattag taataatctt atagagagca cagcaatat tatcggtaat | 480 |
| gaaaatagtt gttattcgga tcccgcgtcc ccatcaggag cgtggtgcgt tgacaatcaa | 540 |
| aatacgctca ttggcagtga taacaatacg atcactggtg cgctgaatgg tcttcacaac | 600 |
| agtcataaca atgatattat tgctagctct gtaaataatt taatggatac gcataataat | 660 |
| attatcgcgg gagggcacta caacaccatt agtggtggtg aaacaatga cattttttggg | 720 |
| agtgaaaaca atgttactga cagcaccgac gccaatatca atggtagtaa taactacgtg | 780 |
| atagatggga atggaattgg tcgagatgat ttgactgaag ataactctat attgggcggc | 840 |
| tctggcaata tgggcgtggg ggattcagta accgcgatta ccaatagcgt ggtgttcggc | 900 |
| ggtaatacat ctggtaattc aaccggctcc actctgacag attctgtatc ggttagcggc | 960 |
| aacggtacat cggggaataa tgtcgttaat atcggcggag cggcaaacgg taataatagt | 1020 |
| gctagcttag gtacaggctc ggtatcctct gaaggaggaa ttgcattggg tagcggttcg | 1080 |
| attgctacac ggaatgatga actgaatatc ggtgatagac aaattaccag cgttaaaaaa | 1140 |
| ggtgttgaga atacagatac aatcaatgtt agtcagttaa acgatagctt tgatgatgtt | 1200 |
| ctgaatttat caaatgaata ttctgacaac tcttttttcca ctgtcactga aaatataaat | 1260 |
| aattatactg atgcctcatt agatactgtg ttgaatacaa ctggtgaata taccgacaac | 1320 |
| tcaatattat tggttactaa tgaaagcaat aattatactg acaatggcat ggagagtgtt | 1380 |
| agtaattatg caaatatcta tgctgatgaa tctttgttag ctatctataa tgaagaggct | 1440 |
| aattacatgt ctaatcttat agatgtgacg ttaataatg ctaataacta tactgatctt | 1500 |
| tcagttaata ccattatata taccggaaaa caatatacag actctcgaat caatgagtac | 1560 |
| caacgtactt ttaaaaatga attttttaacc tattctaatg aaaatttggg cggttttgat | 1620 |
| aaagatatta atcaaaagca gaaacaatta aacgcgggaa tagcggcgac gatggctgct | 1680 |
| gcggttattc ctcaaaaatc gggttctaaa gtctctattg gtgtcgggct tgcaggatat | 1740 |
| agcgatcaag gcgcaggatc tgtgggagcg atttggcatg taaatcaacg aatcacaatg | 1800 |

```
aatacaacga tgacttacga tactcaacgt ggtgttagtt tattaacggg tttatctatc    1860
ggcatatga                                                             1869
```

<210> SEQ ID NO 3
<211> LENGTH: 273
<212> TYPE: PRT
<213> ORGANISM: Yersinia pestis

<400> SEQUENCE: 3

```
Asp Ser Asp Ser Asn Thr Val Ser Gly Ile Ser Asn Asn Leu Ile Glu
1               5                   10                  15

Ser Asn Ser Asn Ile Ile Gly Asn Glu Asn Ser Cys Tyr Ser Asp Pro
            20                  25                  30

Ala Ser Pro Ser Gly Ala Trp Cys Val Asp Asn Gln Asn Thr Leu Ile
        35                  40                  45

Gly Ser Asp Asn Asn Thr Ile Thr Gly Ala Leu Asn Gly Leu His Asn
    50                  55                  60

Ser His Asn Asn Asp Ile Ile Ala Ser Ser Val Asn Asn Leu Met Asp
65                  70                  75                  80

Thr His Asn Asn Ile Ile Ala Gly Gly His Tyr Asn Thr Ile Ser Gly
                85                  90                  95

Gly Gly Asn Asn Asp Ile Phe Gly Ser Glu Asn Asn Val Thr Asp Ser
            100                 105                 110

Thr Asp Ala Asn Ile Asn Gly Ser Asn Asn Tyr Val Ile Asp Gly Asn
        115                 120                 125

Gly Ile Gly Arg Asp Asp Leu Thr Glu Asp Asn Ser Ile Leu Gly Gly
    130                 135                 140

Ser Gly Asn Met Gly Val Gly Asp Ser Val Thr Ala Ile Thr Asn Ser
145                 150                 155                 160

Val Val Phe Gly Gly Asn Thr Ser Gly Asn Ser Thr Gly Ser Thr Leu
                165                 170                 175

Thr Asp Ser Val Ser Val Ser Gly Asn Gly Thr Ser Gly Asn Asn Val
            180                 185                 190

Val Asn Ile Gly Gly Ala Ala Asn Gly Asn Asn Ser Ala Ser Leu Gly
        195                 200                 205

Thr Gly Ser Val Ser Ser Glu Gly Gly Ile Ala Leu Gly Ser Gly Ser
    210                 215                 220

Ile Ala Thr Arg Asn Asp Glu Leu Asn Ile Gly Asp Arg Gln Ile Thr
225                 230                 235                 240

Ser Val Lys Lys Gly Val Glu Asn Thr Asp Thr Ile Asn Val Ser Gln
                245                 250                 255

Leu Asn Asp Ser Phe Asp Asp Val Leu Asn Leu Ser Asn Glu Tyr Ser
            260                 265                 270

Asp
```